United States Patent [19]

Fung et al.

[11] Patent Number: 4,691,061

[45] Date of Patent: Sep. 1, 1987

[54] OXIDATION OF ACETOVANTILLONE TO VANILLIN

[75] Inventors: Bill S. K. Fung, Renton; Bjorn F. Hrutfiord, Seattle, both of Wash.

[73] Assignee: Monsanto Company, St. Louis, Mo.

[21] Appl. No.: 905,618

[22] Filed: Sep. 10, 1986

[51] Int. Cl.$^4$ ............................................. C07C 45/32
[52] U.S. Cl. .................................................... 568/432
[58] Field of Search ........................................ 568/432

[56] References Cited

U.S. PATENT DOCUMENTS

| | | | |
|---|---|---|---|
| 2,692,291 | 10/1954 | Bryan | 568/432 |
| 3,600,442 | 4/1971 | Gitchel et al. | 568/432 |
| 3,686,322 | 8/1972 | Diddams et al. | 568/432 |
| 3,790,637 | 2/1974 | Yang | 568/432 |
| 4,075,248 | 2/1978 | Marshall et al. | 568/432 |

OTHER PUBLICATIONS

Ishikawa et al., Chemical Abstracts, vol. 62 (1965) 12010Q–12011a.

*Primary Examiner*—Werren B. Lone
*Attorney, Agent, or Firm*—Morgan & Finnegan

[57] ABSTRACT

Vanillin is produced from alkaline oxidation treatment of acetovanillone or acetovanillone-rich internal waste streams of lignin processes without the need for utilizing nitrobenzene as an oxidizing agent.

15 Claims, No Drawings

OXIDATION OF ACETOVANTILLONE TO VANILLIN

FIELD OF THE INVENTION

This invention relates generally to alkaline oxidation of p-hydroxy aromatic 1-carbonyl compounds to their corresponding aromatic aldehydes. In particular, this invention relates to the alkaline oxidation of acetovanillone to produce vanillin.

BACKGROUND OF THE INVENTION

Vanillin can be manufactured by a number of synthetic methods. One of the most utilized methods which involves oxidative alkaline hydrolysis of spent sulfite liquor, is called the lignin process. Lignin is an amorphous polymeric substance related to cellulose that together with cellulose forms the woody cell walls of plants and the cementing material between those cell walls. In the lignin process vanillin is produced by a copper catalyzed, alkaline air oxidation of lignosulfonates which are the predominant material of fermented spent-waste liquors from sulfite pulp mills. A major by-product of this lignin process is acetovanillone. Prior to the present invention, acetovanillone was treated as an impurity of the lignin process for vanillin. Acetovanillone was separated and either discarded or used as a pharmaceutical intermediate, food preservative or sunscreening agent. Crude vanillin containing small amounts of acetovanillone as an impurity has also been available commercially, e.g. as a substitute for pure vanillin for many chemical purposes.

Attempts have been made to convert acetovanillone into vanillin; however, heretofore, the only method of doing so involved the use of nitrobenzene. Such a method was first reported in an article entitled "A New Vanillin Synthesis" by Henry O. Mottern, *Canadian Journal of Chemistry*, 56:2107–2108(1934). Unfortunately, nitrobenzene reduces to nitrosobenzene which in turn reduces to phenylhydroxylamine which reduces to aniline along with certain ortho and para azo benzenes. Such compounds are considered undesirable because of their carcinogenic behavior. Accordingly, the nitrobenzene oxidation of acetovanillone to vanillin has not been commercially adopted.

Other methods have also been tried. See, the *Canadian Journal of Chemistry*, 45:3009–3011(1967) which reports the use of various oxidizing agents, particularly cupric oxide, in the oxidation of acetovanillone. This method, however, produced very little, if any, vanillin.

It is an object of the present invention to produce vanillin from acetovanillone without the need to introduce nitrobenzene as an oxidizing agent.

It is a further object of the present invention to provide a method for recycling internal plant streams of the lignin process where such streams are rich in acetovanillone and to produce additional vanillin from said internal streams.

These objects and others are attained by a process which provides for oxidation of acetovanillone with either air or air enriched with oxygen in the presence of an alkaline material. Such oxidation is effected in a medium substantially devoid of nitrobenzene.

DETAILED DESCRIPTION OF THE PREFERRED EMBODIMENTS

In the process of this invention, pure acetovanillone and/or waste streams from the vanillin process, which are composed substantially of acetovanillone, may be used as raw materials. The vanillin processes which have waste streams rich in acetovanillone may include processes which treat parts of coniferous trees. In such processes, coniferon may be extracted, then oxidized and finally hydrolyzed to vanillin, leaving certain waste streams rich in acetovanillone.

Alternatively, the process may begin with papermill waste liquors. This involves controlled oxidation of lignosulfonates, usually attained from the waste sulfite liquors. These waste sulfite liquors are oxidized by contacting with air and sodium hydroxide in a reactor, for example as taught in U.S. Pat. No. 2,692,291, incorporated herein by reference.

A crude product, containing very dilute vanillin, may then be extracted from lignin salts with a solvent, such as, for example 1-butanol. The crude product in butanol solution is then extracted with an aqueous solution of sodium bisulfite. The aqueous phase containing vanillin is then treated with sulfuric acid and air in a blow tower to produce crude vanillin. The crude vanillin is then subjected to vacuum distillation to remove high boiling impurities. Purified vanillin is obtained by multiple crystallization which provides acetovanillone in a waste stream.

More particularly, U.S. Pat. No. 3,600,442, incorporated herein by reference, teaches treating the crystallized liquors with an alkali metal hydroxide and a zinc or magnesium salt to precipitate vanillin and acetovanillone. The vanillin is then separated from the acetovanillone.

Alternatively, U.S. Pat. No. 3,686,322, incorporated herein by reference, discloses that hot hydrocarbon solvents, such as toluene, may be employed to extract vanillin from lignin liquor, after which the solvent is cooled to crystallize the vanillin. The residue after extraction is rich in acetovanillone.

Such streams containing residual acetovanillone after separation of the vanillin are preferred starting materials for the process of this invention.

The acetovanillone is subjected to alkaline oxidation with air or with air enriched with oxygen in the presence of a strong alkaline material as for example a hydroxide of an alkali or alkaline earth metal, preferably sodium hydroxide. We have found that by controlling the amount of alkaline material, e.g. as the equivalent weight ratio of sodium hydroxide to acetovanillone at a range of at least about 3.5 to 1 preferably between 3.5 to 1 and 4.0 to 1, commercially acceptable conversions of acetovanillone to vanillin may be accomplished. Ratios higher than 4.0 to 1 may be employed, however, we have not discovered any substantial improvement of the yield at such ratios. Ratios of sodium hydroxide to acetovanillone of lower than about 3.5 to 1 down to about 2.5 to 1 are useful but not as advantageous in bringing about commercially acceptable yields.

The conversion is preferably carried out at temperatures of at lease about 150° C. to as high as about 200° C. Additionally, the process of this invention is preferably conducted at a pressure of at least about 700 KPa, more preferably in the range of about 900–1200 KPa. Preferably, the time of conversion is at least about 2 hours and may range as high as about 4 hours. It is especially preferred to treat the material for 3 hours.

Catalysts such as sulfates and oxides of the transition elements, copper, manganese, iron, etc. may be employed; however, no appreciable catalytic affect has been observed to improve the conversion yields.

Air may be employed to oxidize the acetovanillone in this invention. Preferably air enriched with oxygen is utilized for purposes of economy and efficient conversion. More preferably, air enriched to about 40% (by volume) oxygen has been observed to improve the yield over the use of air alone by as much as 40 to 50%.

The following examples are intended to illustrate the practice of this invention without unduly limiting its scope.

EXAMPLES 1-25

Two-gram samples of acetovanillone were separately placed in a batch type reactor vessel with 100 gr of 2N NaOH so that the ratio of NaOH to acetovanillone was 4:1. The reactor vessel was heated to about 180° C. and pressurized with either air or air enriched to 40% oxygen to the pressures indicated in Table 1. The reaction was allowed to proceed for the time indicated in Table 1. In some cases, as indicated in Table 1, sulfates and oxides of the transition elements copper, manganese and iron were employed as catalyst and in one case sodium-m-nitrobenzene sulfonate abbreviated as NAMNO. The resulting oxidation products were analyzed by gas chromatography and yields of vanillin (Van), are reported in Table 1.

TABLE 1

| Example | Press. (KPa) | Time (Hour) | Catalyst Type/Amount (Gm) | Vanillin Yield (gm) | Oxidizing Agent | Vanillin Yield (%) |
|---|---|---|---|---|---|---|
| 1 | 1140 | 3 | None | 0.31 | Air | 32 |
| 2 | 1140 | 3 | MnSo4/0.10 | 0.29 | Air | 30 |
| 3 | 1140 | 3 | CuSO4 0.10 | 0.34 | Air | 35 |
| 4 | 1000 | 2 | CuSO4 0.05 | 0.16 | Air | 16 |
| 5 | 1000 | 2 | CuSO4 0.10 | 0.16 | Air | 17 |
| 6 | 1000 | 2 | CuSO4/0.10 | 0.16 | Air | 16 |
| 7 | 1140 | 2½ | CuSO4/0.10 | 0.27 | Air | 27 |
| 8 | 1140 | 3 | None | 0.28 | Air | 29 |
| 9 | 1140 | 3 | None | 0.30 | Air | 30 |
| 10 | 1140 | 3 | None | 0.27 | Air | 27 |
| 11 | 1140 | 3 | MnSO4/0.10 | 0.27 | Air | 27 |
| 12 | 1140 | 3 | CuSO4/0.10 | 0.29 | Air | 29 |
| 13 | 1140 | 3 | CuSO4/0.10 | 0.33 | Air | 34 |
| 14 | 1140 | 3 | CuSO4/0.10 | 0.43 | 40% $O_2$ | 43 |
| 15 | 1140 | 3 | None | 0.43 | 40% $O_2$ | 43 |
| 16 | 1140 | 3 | None | 0.44 | 40% $O_2$ | 45 |
| 17 | 1140 | 2⅓ | CuSO4/0.10 | 0.35 | 40% $O_2$ | 35 |
| 18 | 1140 | 3 | NAMNO/0.10 | 0.31 | Air | 31 |
| 19 | 1140 | 3 | Fe2SO4/0.10 | 0.24 | Air | 24 |
| 20 | 1140 | 3 | CuO/0.10 | 0.32 | Air | 33 |

TABLE 1-continued

| Example | Press. (KPa) | Time (Hour) | Catalyst Type/Amount (Gm) | Vanillin Yield (gm) | Oxidizing Agent | Vanillin Yield (%) |
|---|---|---|---|---|---|---|
| 21 | 1000 | 7 | None | 0.24 | Air | 24 |
| 22 | 1140 | 3 | CuSO4/0.10 | 0.42 | 40% $O_2$ | 42 |
| 23 | 1140 | 4 | None | 0.40 | 40% $O_2$ | 40 |
| 24 | 1140 | 3 | CuSO4/0.50 | 0.28 | Air | 28 |
| 25 | 1275 | 3 | None | 0.36 | Air | 36 |

What we claim is:

1. A process for the production of vanillin comprising contacting (a) p-hydroxy aromatic 1-carbonyl compounds comprising substantially acetovanillone, (b) oxygen and (c) alkaline material.

2. The method of claim 1 wherein the contacting occurs under a pressure of at least 1000 KPa.

3. The method of claim 1 wherein oxygen is provided in the form of air.

4. The method of claim 1 wherein oxygen is in admixture with air and oxygen forms at least 40% of the mixture.

5. The method of claim 1 wherein the alkaline material is present in an equivalent weight ratio of sodium hydroxide to acetovanillone of at least 3.5 to 1.

6. The method of claim 1 wherein the alkaline material is sodium hydroxide.

7. The method of claim 2 wherein the temperature is at least about 165° C.

8. A process for converting acetovanillone to vanillin comprising contacting acetovanillone with oxygen and sodium hydroxide wherein the equivalent weight ratio of sodium hydroxide to acetovanillone is at least about 2.5 to 1.

9. A method of producing vanillin comprising oxidizing acetovanillone with air or with air enriched with oxygen in the presence of an alkaline material in a medium substantially devoid of nitrobenzene.

10. The method of claim 9 wherein the conversion is carried out at a temperature between about 150° C. and about 200° C.

11. The method of claim 9 wherein the conversion is carried out at a pressure of at least about 700 KPa.

12. The method of claim 11 wherein the pressure is between about 900 KPa and about 1200 KPa.

13. The method of claim 9 wherein the time of conversion is between about two hours and about four hours.

14. The method of claim 9 wherein the vanillin yield is between about 16% and about 45%.

15. The method of claim 9 wherein the conversion is carried out at a temperature between about 150° C. and about 200° C., a pressure of at least 700 KPa, for a time period between about two hours and about four hours.

* * * * *